(12) United States Patent
Schmidt et al.

(10) Patent No.: US 10,125,261 B2
(45) Date of Patent: *Nov. 13, 2018

(54) PEARLESCENT PIGMENTS ON THE BASIS OF FINE AND THIN SYNTHETIC SUBSTRATES

(75) Inventors: Ulrich Schmidt, Hersbruck (DE); Michael Gruner, Auerbach (DE); Dirk Schumacher, Pegnitz (DE); Gunter Kaupp, Neuhaus (DE); Barbara Mendler, Meersburg (DE)

(73) Assignee: ECKART GMBH, Hartenstein (DE)

( * ) Notice: Subject to any disclaimer, the term of this patent is extended or adjusted under 35 U.S.C. 154(b) by 465 days.

This patent is subject to a terminal disclaimer.

(21) Appl. No.: 13/501,497

(22) PCT Filed: Oct. 10, 2010

(86) PCT No.: PCT/EP2010/006237
§ 371 (c)(1),
(2), (4) Date: Apr. 19, 2012

(87) PCT Pub. No.: WO2011/045030
PCT Pub. Date: Apr. 21, 2011

(65) Prior Publication Data
US 2012/0219607 A1     Aug. 30, 2012

(30) Foreign Application Priority Data
Oct. 14, 2009   (DE) .......................... 10 2009 049 413

(51) Int. Cl.
*A61K 8/29*       (2006.01)
*A61Q 1/08*       (2006.01)
(Continued)

(52) U.S. Cl.
CPC .............. *C09C 1/0021* (2013.01); *A61K 8/29* (2013.01); *A61Q 19/00* (2013.01);
(Continued)

(58) Field of Classification Search
None
See application file for complete search history.

(56) References Cited

U.S. PATENT DOCUMENTS 3,861,946 A * 1/1975 Waitkins ............... C01F 11/466
                                                        106/415
5,266,107 A * 11/1993 Hoffman ....................... 106/415
(Continued)

FOREIGN PATENT DOCUMENTS

DE        19618569 A1    11/1997
DE        19727767 A1    1/1999
(Continued)

OTHER PUBLICATIONS

SunSHINE color Effect Pigments, Maprecos 2013 Catalogue, front matter and pp. 63-64, accessed online at http://www.maprecos.com/wp-content/uploads/2013/01/CATALOGUE-2013-VERSION-ELECTRONIQUE.pdf on Jul. 12, 2013.*
(Continued)

*Primary Examiner* — Bethany P Barham
*Assistant Examiner* — Dominic Lazaro
(74) *Attorney, Agent, or Firm* — The Webb Law Firm

(57) ABSTRACT

The invention relates to pearlescent pigments comprising a largely transparent platelet-shaped synthetic substrate having a density $\rho_S$ and at least one optically active coating having a density $\rho_M$, the substrate having an average size $d_{50}$ from a range from 2.0 μm to 8.0 μm and an average height $h_S$ from a range from 40 nm to 110 nm and the total lead content of the pearlescent pigments is ≤10 ppm. The invention further relates to a method for producing the pearlescent pigments, and also to the use thereof.

18 Claims, 2 Drawing Sheets

Substrate S and Coating M

(51) Int. Cl.
  *A61Q 1/04* (2006.01)
  *A61K 8/02* (2006.01)
  *C08K 3/34* (2006.01)
  *A61Q 1/10* (2006.01)
  *C09C 1/00* (2006.01)
  *A61Q 19/00* (2006.01)
  *A61Q 1/02* (2006.01)
  *A61Q 3/02* (2006.01)

(52) U.S. Cl.
  CPC .......... *A61K 2800/436* (2013.01); *A61Q 1/02* (2013.01); *A61Q 1/10* (2013.01); *A61Q 3/02* (2013.01); *C01P 2006/62* (2013.01); *C01P 2006/80* (2013.01); *C09C 2200/102* (2013.01); *C09C 2200/1004* (2013.01); *C09C 2200/301* (2013.01); *C09C 2200/302* (2013.01); *C09C 2220/106* (2013.01)

(56) References Cited

U.S. PATENT DOCUMENTS

| | | | |
|---|---|---|---|
| 5,741,355 A * | 4/1998 | Yamamoto | A61K 8/11 106/417 |
| 6,019,831 A | 2/2000 | Schmidt et al. | |
| 6,294,592 B1 | 9/2001 | Herrmann et al. | |
| 6,689,205 B1 | 2/2004 | Bruckner et al. | |
| 7,413,599 B2 | 8/2008 | Henglein et al. | |
| 7,699,927 B2 | 4/2010 | Henglein et al. | |
| 2003/0147819 A1* | 8/2003 | Watanabe | 424/63 |
| 2004/0096579 A1* | 5/2004 | Kil-Wan et al. | 427/212 |
| 2005/0013934 A1 | 1/2005 | Xiong et al. | |
| 2005/0176580 A1 | 8/2005 | Osaka et al. | |
| 2005/0176850 A1* | 8/2005 | Schmidt et al. | 523/160 |
| 2006/0042508 A1 | 3/2006 | Henglein et al. | |
| 2006/0042509 A1* | 3/2006 | Henglein et al. | 106/415 |
| 2006/0111466 A1 | 5/2006 | Bujard et al. | |
| 2006/0223910 A1 | 10/2006 | Bagala, Sr. | |
| 2007/0199478 A1 | 8/2007 | Schlegl et al. | |
| 2008/0017075 A1* | 1/2008 | Cao et al. | 106/418 |
| 2008/0017076 A1 | 1/2008 | Noguchi | |
| 2008/0181921 A1 | 7/2008 | DeLuca | |
| 2009/0258251 A1* | 10/2009 | Abe et al. | 428/702 |
| 2009/0311209 A1 | 12/2009 | Bujard | |
| 2010/0255047 A1 | 10/2010 | Anselmann et al. | |
| 2010/0298469 A1 | 11/2010 | Kaupp et al. | |
| 2011/0064779 A1 | 3/2011 | Gruener et al. | |
| 2011/0226161 A1 | 9/2011 | Schumacher et al. | |
| 2011/0259243 A1 | 10/2011 | Schumacher et al. | |
| 2011/0265689 A1 | 11/2011 | Schumacher et al. | |
| 2011/0265690 A1 | 11/2011 | Schumacher et al. | |
| 2012/0027830 A1 | 2/2012 | Nakamura et al. | |

FOREIGN PATENT DOCUMENTS

| | | | |
|---|---|---|---|
| DE | 10315775 A1 | 10/2004 | |
| DE | 102004041592 A1 | 3/2006 | |
| DE | 60318235 T2 | 12/2008 | |
| DE | 102007041027 A1 | 3/2009 | |
| EP | 0723997 B1 | 6/1999 | |
| EP | 1072651 A1 | 1/2001 | |
| EP | 1554345 B1 | 7/2005 | |
| EP | 1564261 A2 | 8/2005 | |
| EP | 1 595 921 A1 | 11/2005 | |
| EP | 1682622 A1 | 7/2006 | |
| EP | 1727864 A1 | 12/2006 | |
| JP | 09-255891 | 9/1997 | |
| JP | 2000-281932 | 10/2000 | |
| JP | 2001262036 A | 9/2001 | |
| JP | 200238051 A | 2/2002 | |
| JP | 2002-294098 | 10/2002 | |
| JP | 2003080836 A | 3/2003 | |
| JP | 2005314649 A | 11/2005 | |
| JP | 2006-124524 | 5/2006 | |
| JP | 2006-527779 A | 12/2006 | |
| JP | 2007-126643 A | 5/2007 | |
| JP | 2008-510866 A | 4/2008 | |
| JP | 200888317 A | 4/2008 | |
| JP | 2008-546880 A | 12/2008 | |
| JP | 2011516706 A | 5/2011 | |
| WO | 2002/090448 A3 | 11/2002 | |
| WO | 2004/087816 A2 | 10/2004 | |
| WO | 2006021388 A1 | 3/2006 | |
| WO | 2007/054379 A1 | 5/2007 | |
| WO | 2009010288 A2 | 1/2009 | |
| WO | 2009030293 A2 | 3/2009 | |
| WO | WO 2009103322 A1 * | 8/2009 | .......... A61K 8/0229 |
| WO | 2009/127406 A1 | 10/2009 | |
| WO | 2009127406 A1 | 10/2009 | |
| WO | WO 2009127406 A1 * | 10/2009 | |
| WO | 2010113899 A1 | 10/2010 | |

OTHER PUBLICATIONS

Pfaff et al. Chemistry Reviews, 99: 1963-1981 (1999).*
Horiba Scientific, "Understanding Particle Size Distribution Calculations", accessed at http://www.horiba.com/us/en/ scientific/ products/ particle-characterization/education/general-information/data-interpretation/ understanding-particle-size-distribution-calculations/, on Aug. 6, 2015.*
Docekal et al., Spectrochemica Acta Part B 62: 304-308 (2007).*
Translation of JP, 2000-281932, accessed in opposition proceedings of EB2123721B1 from EPO.*
Ryu et al., Journal of Industrial and Engineering Chemistry, 14: 213-218 (2008).*
"Iron Oxides", 21 CFR 73.2250, revised as of Apr. 1, 2005.*
"Cilas 1064", brochure, accessed at http://www.es-france.com/pdf/ 1064 _us_doctech.pdf, accessed Jul. 31, 2017.*
Google Patent Machine translation, Kaupp et al. WO 2009103322 A1, dowloaded Sep. 18, 2017.*
R. C. Weast, S. M. Selby, C. D. Hodgman, Handbook of Chemistry and Physics, 45th edition (1964-1965).
C. Schmidt, M. Friz, Optical Physics of Synthetic Interference Pigments, Kontakte (Darmstadt) 1992 (2) S. 15-24.
F. Hofmeister and Harry Pieper, Reflectance Measurements of Interference, Aluminum, and Masstone Pigments, Article from farbe + lack, vol. 95, Aug. 1989, Research and Development section (in German together with English translation).
Notice of Reasons for Rejection dated Jan. 29, 2013 in corresponding Japanese Patent Application No. 2011-504373 (with English language translation).
International Search Report dated Jul. 22, 2009, issued in corresponding International Application No. PCT/EP2009/002757.
European Search Report dated Aug. 19, 2008, issued in corresponding European priority Application No. EP08007357.0.
German Examination Report dated Mar. 3, 2010 in corresponding German Patent Application No. 10 2009 031 266.8-43.
International Search Report dated Dec. 21, 2010, issued in corresponding International Application No. PCT/EP2010/EP2010/ 003740 (with English language translation).
Nancy M. Hepp et al., "Determination of total lead in lipstick: Development and validation of a microwave-assisted digestion, inductively coupled plasma-mass spectrometric method", J. Cosmet. Sci, Jul./Aug. 2009, 405-414, 60.
C. Schmidt et al., "Optical Physics of Synthetic Interference Pigments", Kontakte (Darmstadt), 1992, 15-24, (2).
Franz Hofmeister et al., "Reflectance measurements of interference, aluminum, and masstone pigments", farbe + lack, Aug. 1989, 557-560, vol. 95, Research & Development section.
"Color Additives and Cosmetics" taken from U.S. Food and Drug Association website: https:I/www.fda.gov/forindustry/coloradditives/ coloradditivesinspecificproducts/incosmetics/ucm110032.thm with effective update date of Apr. 29, 2007.
"The whitier white effect pigment", BASF Brochure for GlacierTM Frost White, currently available at: https://product-finder-basf.com/ group/corporate/productfinder/de/literature-document:/Brand+Glacier-Brochure-The+whiter+white+effect+pigment+GlacierTM+Frost+ White-English.pdf of Nov. 14, 2007.

(56) References Cited

OTHER PUBLICATIONS

Pfaff G. et al., Special Effects Pigments—Technical Basics and Applications, 2nd revised edition, 2008—pp. 40-41.
Technical Data Sheet, Material No. 035623ZZ5 from Eckart GmbH dated Apr. 24, 2015 for the product SYMIC E001.

* cited by examiner

Fig. 1: Substrate S and Coating M

PEARLESCENT PIGMENTS ON THE BASIS OF FINE AND THIN SYNTHETIC SUBSTRATES

BACKGROUND OF THE INVENTION

Field of the Invention

The invention relates to pearlescent pigments based on largely transparent platelet-shaped synthetic substrates, to their use and preparation, and to coating compositions which comprise the pearlescent pigments of the invention.

Description of Related Art

EP 0 723 997 B1 describes a flakelike pigment with a pearllike luster that comprises a synthetically produced fluorophlogopite mica coated with metal oxide. The synthetically produced fluorophlogopite mica has an average refractive index which does not exceed the figure 1.58, an iron content with a weight fraction of not more than 0.1% by weight, and a pearl parameter, i.e., specific volume (A)× gloss value of the powder (B), ≥10. Such pigments are said to have a reduced yellow tinge and an improved interference effect.

Interference pigments based on transparent, platelet-shaped substrates, coated with a high-index coating consisting of titanium dioxide, are described in EP 1 564 261 A2. The platelet-shaped substrates have an average thickness of between 0.02 µm and 2 µm, preferably between 0.1 µm and 1 µm, and more preferably between 0.2 µm and 0.8 µm. For the attainment of an intense color effect with a superimposed, angle-dependent hue, the average thickness of the individual platelets must be situated within a standard deviation of ≤15%.

In EP 1 072 651 A1, pigments are described that are based on thin flakes having an average particle size of 0.5 µm to 10 µm, preferably 2 µm to 8 µm, which are coated first with spherical $SiO_2$ particles and thereafter with ultrafine titanium dioxide particles. Pigments of this kind are added for reasons including their soft-focus effect, as fillers, to cosmetic formulations, for example. As a result of the spherical structure of the $SiO_2$ and $TiO_2$ particles, the reflection is substantially undirected, which in the cosmetic application, on the skin, evokes an unwanted whitening effect.

The aforementioned pearlescent pigments are put to uses including the pigmentation of cosmetics. A disadvantage is that these known pearlescent pigments do not have a sufficient soft-focus effect—that is, within a cosmetic, they do not have the capacity to provide satisfactory concealment of creases or irregularities in the skin, without at the same time evoking an unwanted whitening effect. Furthermore, standard commercial pearlescent pigments have a measurable lead content, which is undesirable in cosmetic formulations.

Instances of contamination by heavy metals in cosmetic formulations are unwanted in the interests of the consumer. Elevated lead levels, in particular, in cosmetic formulations have come under criticism in more recent times. Color additives are monitored for their lead content by the FDA, and must not exceed a limit of 20 µg/g. Other cosmetic ingredients are subject, in terms of lead content, to the responsibility of the manufacturers (Nancy M. Hepp, William R. Mindak, John Cheng, *J. Cosmet. Sci.*, 60, 405-414 (July/August 2009)).

There exists, accordingly, a need for improved pearlescent pigments having an extremely low total lead content. A particular desire is for provision of pearlescent pigments having improved soft focus and a pleasant feeling on the skin. These pearlescent pigments shall combine the properties of conventional pearlescent pigments, such as interference, deep gloss, and coloredness where appropriate, with an additional soft-focus effect.

The pearlescent pigments, lastly, ought to have good opacity with strong haze effect and also, at the same time, an intense interference color.

SUMMARY OF THE INVENTION

The object on which the invention is based is achieved through the provision of pearlescent pigments comprising a largely transparent platelet-shaped synthetic substrate having a density $\rho_S$ and at least one optically active coating having a density $\rho_M$, the substrate having an average size $d_{50}$ from a range from 2.0 µm to 8.0 µm and an average height $h_S$ from a range from 40 nm to 110 nm and the total lead content of the pearlescent pigments being ≤10 ppm.

Preferred developments of the pearlescent pigments of the invention are specified in dependent claims 2 to 7.

The object on which the invention is based is also achieved by a method for producing the pearlescent pigments of the invention, which comprises the following steps:

a) classifying the largely transparent platelet-shaped synthetic substrate, to give a substrate having an average height $h_S$ from a range from 40 nm to 110 nm, b) coating the classified largely transparent platelet-shaped synthetic substrate with at least one optically active, preferably high-index, layer, to give a pearlescent pigment having an average size $d_{50}$ from a range from 2.1 µm to 8.6 µm.

Furthermore, the object of the invention is also achieved by the use of the pearlescent pigments of the invention in paints, printing inks, inkjet inks, toners, cosmetics, plastics, textiles, glass, enamel, glazes or ceramic.

The object on which the invention is based is also achieved through provision of a coating composition, more particularly a cosmetic product, which comprises the pearlescent pigments of the invention.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
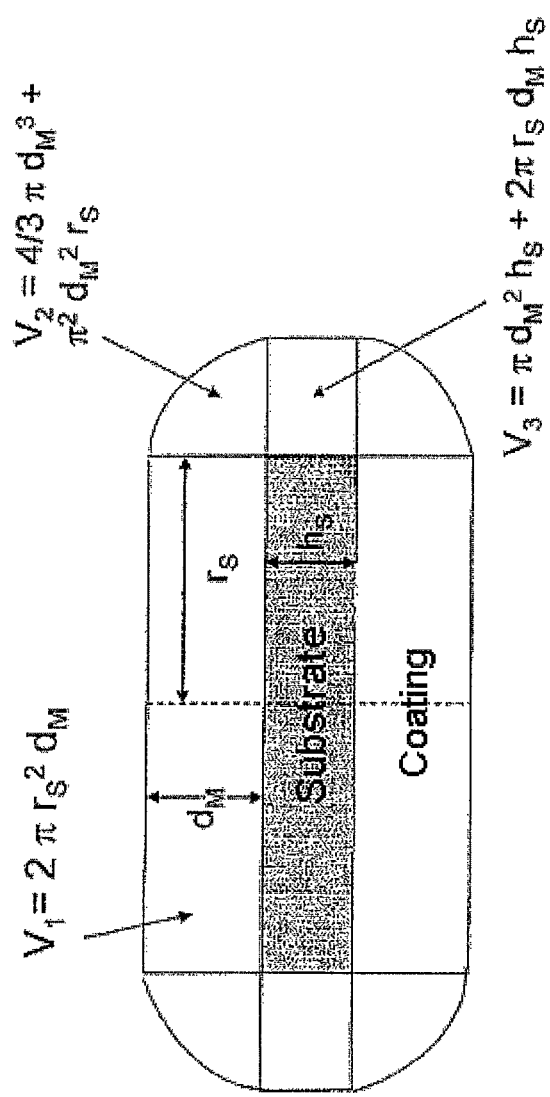
FIG. 1 is an illustration of the model used to calculate $V_m$, the volume of the coating material.

The terms "coating" and "layer" are used interchangeably in the context of the present invention.

The inventors have surprisingly found that pearlescent pigments based on largely transparent platelet-shaped synthetic substrates have a good soft-focus effect and a good feeling on the skin when the $d_{50}$ value of the size and the average height $h_S$ are each located within the range of values indicated above.

The pearlescent pigments of the invention, then, have a substrate with an extraordinarily small diameter and an extraordinarily small substrate thickness. It has surprisingly emerged that, when these substrates are used for producing pearlescent pigments, pearlescent pigments are obtained that have a good soft-focus effect and a pleasant feeling on the skin.

At the same time, the pearlescent pigments of the invention, in spite of the small diameter, have strong interference colors, and so the pearlescent pigments of the invention are especially suitable for the coloring of cosmetics.

Cosmetics comprising the pearlescent pigments of the invention are notable, in makeup, for example, by the imparting of a homogeneous appearance. On account of the transparency of the pearlescent pigments of the invention, the skin is endowed with a natural appearance with no masking effect. The low particle size of the pearlescent pigments of the invention prevents unwanted shine, while at the same time providing opacity and, if desired, coloredness.

It has also emerged, surprisingly, that the pearlescent pigments of the invention, when used in cosmetics, adhere more reliably to the base, such as skin, eyelids, hair, lashes, fingernails and/or toenails, despite the area of contact with the base being smaller because of the smaller diameter of the pearlescent pigment.

In light of this surprising result in the context of adhesion to the base, it is now supposed that, with larger pearlescent pigments, the pigments do not lie on the base over their full area, and hence sections of these larger pearlescent pigments "stick out" above the base and, under exposure to mechanical forces, as for example on blinking or muscular movements, or under the influence of liquids, such as water or bodily secretions, such as perspiration, for example, larger pearlescent pigments are detached more readily from the base. A more mature or older skin, in particular, has relatively greater irregularities, at which the pearlescent pigments of the invention are presumably able to adhere over their full area, or with a larger relative area fraction, than—presumably—larger pearlescent pigments are able to achieve.

In the case of hairs or lashes, which typically have a thickness in the range from 40 μm to 120 μm, the pearlescent pigments of the invention, taking into account the curvature of the hairs as well, lie presumably largely against the hairs or lashes over the full area of the pigments. Surprisingly, therefore, the pearlescent pigments of the invention have a very good hold to hairs and lashes, and so do not drop off during combing or during ruffling of hairs, as in the wind, for example. If the pearlescent pigments were to drop off it would be extremely deleterious, since on the one hand the hairs or lashes would no longer have the desired uniform coloration, and on the other hand the visual effect produced would be that of dandruff, as a result, for example, of deposition of the dropped-off pearlescent pigments in the shoulder region of a dress or suit.

By an optically active coating is meant in accordance with the invention, for example, semitransparent metal layers. The layer thickness of the semitransparent metal layers is situated typically in a range from 5 nm to 30 nm, preferably in a range from 10 nm to 25 nm. Layer thicknesses from a range from 20 nm to 25 nm as well have proven very suitable.

Furthermore, by an optically active coating is meant, in accordance with the invention, metal oxide layers, preferably high-index metal oxide layers. The refractive index of high-index metal oxide layers is preferably above 1.8, more preferably above 2.0. Refractive indices of more than 2.2 or more than 2.6 as well have proven very suitable. The average geometric layer thickness of the high-index metal oxide layer is situated preferably in a range between 10 nm and 300 nm, more preferably in a range between 20 nm and 200 nm, more preferably still in a range between 50 nm and 150 nm. Instead of high-index metal oxides it is also possible to use other high-index materials; examples being metal sulfides, metal selenides or metal nitrides, with the geometric layer thicknesses preferably exhibiting the ranges specified for the high-index metal oxides.

According to one very preferred embodiment of the invention, the optically active coating is one (number: 1) high-index metal oxide layer.

It will be appreciated that more than one high-index metal oxide layer may also be applied to the substrate.

In the case of this variant, it is preferred for there to be disposed, between two high-index metal oxide layers, at least one low-index layer, with a refractive index preferably of less than 1.8, more preferably of less than 1.6.

As a low-index layer it is preferred to use low-index metal oxide layers, more particularly silicon oxide and/or aluminum oxide.

Low-index layers used are preferably layers of silicon oxide, preferably $SiO_2$, aluminum oxide, preferably $Al_2O_3$, AlOOH, boron oxide, preferably $B_2O_3$, $MgF_2$ or mixtures thereof.

The substrate has an average size $d_{50}$ from a range from 2.0 μm to 8.0 μm, preferably from a range from 2.1 μm to 7.0 μm, more preferably from a range from 2.5 μm to 6.0 μm, and with particular preference from a range from 3.0 μm to 5.0 μm.

Above an average size $d_{50}$ of 8.0 μm, the advantageous properties of the pearlescent pigments of the invention, such as, for example, the adhesion to round surfaces such as lashes, are no longer apparent.

Below an average size $d_{50}$ of 2.0 μm, the advantageous properties of the pearlescent pigments of the invention are no longer apparent, since the increasing number of particles per gram results in an increasing fraction of undirected light scattering and hence in an unwanted whitening effect.

By the average size $d_{50}$ is meant, in the context of this invention, the $d_{50}$ value of the cumulative frequency distribution of the volume-averaged size distribution function, of the kind obtained by laser diffraction methods. In this case, preferably, the size distribution curve is determined using an instrument from the company Quantachrome (instrument: Cilas 1064). The scattered light signals are analyzed here by way of the Fraunhofer method.

The $d_{50}$ value indicates that 50% of the substrate or pigment particles have a diameter which is less than or equal to the specified value—6 μm, for example.

Furthermore, the substrate of the pearlescent pigments of the invention has an average height (layer thickness) $h_S$ from a range from 40 nm to 110 nm, preferably from a range from 40 nm to 100 nm, more preferably from a range from 40 nm to 95 nm, more preferably still from a range from 45 nm to 94 nm, and with particular preference from a range from 50 nm to 90 nm.

Below a layer thickness of 40 nm, the pearlescent pigments are mechanically too fragile, and the coating times with metal or high-index metal oxide last too long, owing to the extremely high specific surface area, to be economically tenable. By the specific surface area is meant the surface area per unit weight. Since the layer thickness of the substrates of the pearlescent pigments of the invention is extremely low, these substrates have a very large surface area per unit weight by comparison with conventional substrates.

Above a layer thickness of 110 nm, the advantages of the invention are barely still present.

In another embodiment the pearlescent pigment of the invention has a standard deviation in the substrate height $h_S$ of from 25% to 80%, preferably of from 30% to 60%, and more preferably of from 28% to 50%.

In accordance with one preferred variant of the invention, the pearlescent pigments have a size distribution with a $d_{90}$ value from a range from 5.0 µm to 11.0 µm, preferably from a range from 5.1 µm to 10.0 µm, more preferably from a range from 5.5 µm to 9.0 µm, and with particular preference from a range from 6.0 µm to 8.5 µm.

In accordance with a further variant of the invention, the pearlescent pigments have a size distribution with a $d_{50}$ value from a range from 2.1 µm to 8.6 µm, preferably from a range from 2.2 µm to 7.6 µm, more preferably from a range from 2.6 µm to 6.6 µm, and with particular preference from a range from 3.1 µm to 5.6 µm.

The pearlescent pigments of the invention, accordingly, constitute a new class of pearlescent pigments in the form of extremely fine pearlescent pigments which are based on a largely transparent substrate having a very low average size and a very low average layer thickness. Pigments of this kind exhibit an unusually high scattered-light fraction, owing to the high proportion of edges relative to the area. In paint applications, for example, this results in a high haze effect. Nevertheless, surprisingly, the pearlescent pigments of the invention display an intense interference color, despite the fact that the interference color is usually prevented or greatly attenuated by scattering effects.

The pearlescent pigments of the invention have at least one optically active coating, preferably in the form of a high-index coating, preferably high-index metal oxide layer, and/or a semitransparent metal coating having a density $\rho_M$. By the density $\rho_M$ is meant the density of the optically active coating. Accordingly, in the case of a metal oxide layer, $\rho_M$ is the density of the metal oxide layer and, in the case of a semitransparent metal layer, $\rho_M$ is the density of the semitransparent metal layer.

In the context of this invention, pigments based on largely transparent platelet-shaped synthetic substrates and a semitransparent metal layer are also referred to as pearlescent pigments. The pearlescent pigments of the invention preferably exhibit an interference effect.

Suitable largely transparent platelet-shaped substrates to be coated are nonmetallic, synthetic platelet-shaped substrates. The substrates are preferably essentially transparent: that is, they are at least partially transmissive to visible light.

In accordance with one preferred embodiment of the invention, the largely transparent platelet-shaped synthetic substrates may be selected from the group consisting of synthetic mica, $SiO_2$ platelets, $Al_2O_3$ platelets, polymeric platelets, platelet-shaped bismuth oxychloride, platelet-shaped substrates comprising an inorganic-organic hybrid layer, and mixtures thereof. The largely transparent platelet-shaped synthetic substrates are preferably selected from the group consisting of synthetic mica, $SiO_2$ platelets, $Al_2O_3$ platelets, and mixtures thereof. With further preference the largely transparent platelet-shaped synthetic substrates are selected from the group consisting of $SiO_2$ platelets, $Al_2O_3$ platelets, and mixtures thereof. With further preference the largely transparent platelet-shaped synthetic substrates are selected from the group consisting of synthetic mica, $SiO_2$ platelets, and mixtures thereof. With further preference the largely transparent platelet-shaped synthetic substrates are selected from the group consisting of synthetic mica, $Al_2O_3$ platelets, and mixtures thereof. Especially preferred is synthetic mica. Additionally preferred are $Al_2O_3$ platelets. Likewise preferred are $SiO_2$ platelets.

In contrast to natural substrates such as natural mica, for example, synthetic substrates are substantially free from intercalated extraneous ions, which may alter the shade. Furthermore, as a result of the impurities, the lightness (L* value) may be significantly lowered. This can be determined, for example, by diffuse colorimetry on the respective powder beds using a CR 310 colorimeter from Konica Minolta.

| Synthetic mica | L* = 97.6 |
| Natural mica | L* = 83.6 |

In another embodiment, the largely transparent platelet-shaped synthetic substrates used may have L* values ≥90, preferably ≥92, and more preferably ≥95.

In a further embodiment, the largely transparent platelet-shaped synthetic substrates used may have an iron content of up to 0.2% by weight. The iron content may be situated within a range from 0.01% by weight to 0.2% by weight, preferably in a range from 0.1% by weight to 0.19% by weight, and more preferably in a range from 0.12% by weight to 0.18% by weight. In a further embodiment, the largely transparent platelet-shaped synthetic substrates used may have an iron content of 0.15% by weight to 0.2% by weight.

In another embodiment, the largely transparent platelet-shaped synthetic substrates used may have a refractive index from a range from 1.55 to 1.70, preferably from a range from 1.58 to 1.68, and more preferably from a range from 1.59 to 1.65.

In one preferred embodiment, the pearlescent pigments of the invention have at least one high-index coating. The high-index coating preferably has a refractive index $n_M$>2.0 and more preferably a refractive index $n_M$>2.2.

With particular preference the high-index coating has or is a metal oxide layer and/or a metal hydroxide layer and/or a metal oxide hydrate layer.

High-index layers used are preferably high-index metal oxides, metal hydroxides and/or metal oxide hydrates. Metal oxides used are preferably metal oxides of the group consisting of titanium oxide, iron oxide, cerium oxide, chromium oxide, tin oxide, zirconium oxide, cobalt oxide, and mixtures thereof. Instead of or in addition to the oxides specified above, it will be appreciated that the corresponding metal hydroxides and/or metal oxide hydrates can also be used.

The titanium oxide in this context may be selected from the group consisting of rutile, anatase, and brookite. The titanium oxide is preferably present as $TiO_2$ in the anatase modification.

The iron oxide is preferably selected from the group consisting of hematite, goethite and/or magnetite. The iron oxide is preferably present as $Fe_2O_3$ (hematite) and/or $Fe_3O_4$ (magnetite).

Particular preference is given to $TiO_2$ and $Fe_2O_3$ and also mixtures and combinations thereof. In mixtures of these oxides, the $TiO_2$ is present in a pseudobrookite or pseudorutile modification or alternatively as ilmenite.

$TiO_2$ coated pigments allow the provision of silver shades. These pigments are extremely advantageous for what is called the "immediate whitening effect". This term comprehends cosmetic skin formulations which impart a whiter appearance to the skin. To date, $TiO_2$ pigments have usually been used to achieve this immediate whitening effect. Disadvantageously, the conventional $TiO_2$ pigments often possess what is called a masking effect. Because of the combination of existing gloss and the special fine division, the pigments of the invention permit a more natural effect.

In the case of iron oxides as high-index coating, the pearlescent pigments of the invention can be employed advantageously in hair formulations in particular. Pigments of this kind support the natural hair color and nevertheless, on account of their fineness, do not act as "dandruff". This applies in this case particularly to dark hair, preferably brunette hair. Blonde hair as well can be supported or boosted in its coloring by cosmetic hair products which comprise "golden" or "beige" pearlescent pigments of the invention. Moreover, hair colored red, blue or green can be supported in its coloring by correspondingly colored pearlescent pigments.

As an optically active coating or layer it is also possible, instead of or in addition to the one or more high-index metal oxide layers, for one or more semitransparent metal layers to be applied. In order to produce the semitransparent metal layers, it is preferred to apply one or more metals selected from the group consisting of silver, gold, aluminum, iron, magnesium, chromium, copper, zinc, tin, manganese, cobalt, titanium, tantalum, molybdenum, and mixtures and alloys thereof.

According to one preferred variant of the invention, the pearlescent pigments have a metal oxide layer of $TiO_2$ and a substrate of synthetic mica.

The relationship between the metal oxide in % by weight, based on the total weight of $TiO_2$ and synthetic mica, and the average layer thickness of the $TiO_2$ coating is preferably as follows:

a metal oxide content of 30-80% by weight with an average metal oxide layer thickness of above 20 to 50 nm;
a metal oxide content of 50-85% by weight with an average metal oxide layer thickness of above 50 to 75 nm;
a metal oxide content of 59-89% by weight with an average metal oxide layer thickness of above 75 to 95 nm;
a metal oxide content of 66-92% by weight with an average metal oxide layer thickness of above 95 to 125 nm;
a metal oxide content of 69-96% by weight with an average metal oxide layer thickness of above 125 to 215 nm.

With particular preference, the relationship between the $TiO_2$ content in % by weight, based on the total weight of $TiO_2$ and synthetic mica, and the average layer thickness of the $TiO_2$ coating is as follows:

a $TiO_2$ content of 35-62% by weight with an average $TiO_2$ layer thickness of above 20 to 35 nm;
a $TiO_2$ content of 40-74% by weight with an average $TiO_2$ layer thickness of above 35 to 45 nm;
a $TiO_2$ content of 45-78% by weight with an average $TiO_2$ layer thickness of above 45 to 55 nm;
a $TiO_2$ content of 50-82% by weight with an average $TiO_2$ layer thickness of above 55 to 65 nm;
a $TiO_2$ content of 55-85% by weight with an average $TiO_2$ layer thickness of above 65 to 75 nm;
a $TiO_2$ content of 60-86.5% by weight with an average $TiO_2$ layer thickness of above 75 to 85 nm;
a $TiO_2$ content of 65-88% by weight with an average $TiO_2$ layer thickness of above 85 to 95 nm;
a $TiO_2$ content of 67-89% by weight with an average $TiO_2$ layer thickness of above 95 to 105 nm;
a $TiO_2$ content of 68-90% by weight with an average $TiO_2$ layer thickness of above 105 to 115 nm;
a $TiO_2$ content of 69-91% by weight with an average $TiO_2$ layer thickness of above 115 to 125 nm;
a $TiO_2$ content of 70-92% by weight with an average $TiO_2$ layer thickness of above 125 to 135 nm;
a $TiO_2$ content of 71-92.5% by weight with an average $TiO_2$ layer thickness of above 135 to 145 nm;
a $TiO_2$ content of 72-93% by weight with an average $TiO_2$ layer thickness of above 145 to 155 nm;
a $TiO_2$ content of 73-93% by weight with an average $TiO_2$ layer thickness of above 155 to 165 nm;
a $TiO_2$ content of 73.5-93.5% by weight with an average $TiO_2$ layer thickness of above 165 to 175 nm;
a $TiO_2$ content of 74-94% by weight with an average $TiO_2$ layer thickness of above 175 to 185 nm;
a $TiO_2$ content of 74.5-94% by weight with an average $TiO_2$ layer thickness of above 185 to 195 nm;
a $TiO_2$ content of 75-94.5% by weight with an average $TiO_2$ layer thickness of above 195 to 205 nm;
a $TiO_2$ content of 75.5-95% by weight with an average $TiO_2$ layer thickness of above 205 to 215 nm.

Furthermore, the relationship between the $TiO_2$ content in % by weight, based on the total weight of $TiO_2$ and synthetic mica, and the average layer thickness of the $TiO_2$ coating is preferably as follows:

a $TiO_2$ content from a range of 47.5-62% by weight with an average $TiO_2$ layer thickness from a range from above 20 to 35 nm;
a $TiO_2$ content from a range of 58-74% by weight with an average $TiO_2$ layer thickness from a range from above 35 to 45 nm;
a $TiO_2$ content from a range of 63-78% by weight with an average $TiO_2$ layer thickness from a range from above 45 to 55 nm;
a $TiO_2$ content from a range of 67-82% by weight with an average $TiO_2$ layer thickness from a range from above 55 to 65 nm;
a $TiO_2$ content from a range of 70-85% by weight with an average $TiO_2$ layer thickness from a range from above 65 to 75 nm;
a $TiO_2$ content from a range of 73.5-86.5% by weight with an average $TiO_2$ layer thickness from a range from above 75 to 85 nm;
a $TiO_2$ content from a range of 75-88% by weight with an average $TiO_2$ layer thickness from a range from above 85 to 95 nm;
a $TiO_2$ content from a range of 76.5-89% by weight with an average $TiO_2$ layer thickness from a range from above 95 to 105 nm;
a $TiO_2$ content from a range of 78.5-90% by weight with an average $TiO_2$ layer thickness from a range from above 105 to 115 nm;
a $TiO_2$ content from a range of 80-91% by weight with an average $TiO_2$ layer thickness from a range from above 115 to 125 nm;
a $TiO_2$ content from a range of 81.5-92% by weight with an average $TiO_2$ layer thickness from a range from above 125 to 135 nm;
a $TiO_2$ content from a range of 83-92.5% by weight with an average $TiO_2$ layer thickness from a range from above 135 to 145 nm;
a $TiO_2$ content from a range of 84-93% by weight with an average $TiO_2$ layer thickness from a range from above 145 to 155 nm;
a $TiO_2$ content from a range of 85-93% by weight with an average $TiO_2$ layer thickness from a range from above 155 to 165 nm;
a $TiO_2$ content from a range of 86-93.5% by weight with an average $TiO_2$ layer thickness from a range from above 165 to 175 nm;

a TiO$_2$ content from a range of 87-94% by weight with an average TiO$_2$ layer thickness from a range from above 175 to 185 nm;

a TiO$_2$ content from a range of 87.5-94% by weight with an average TiO$_2$ layer thickness from a range from above 185 to 195 nm;

a TiO$_2$ content from a range of 88-94.5% by weight with an average TiO$_2$ layer thickness from a range from above 195 to 205 nm;

a TiO$_2$ content from a range of 89-95% by weight with an average TiO$_2$ layer thickness from a range from above 205 to 215 nm.

In the case of a further-preferred embodiment, the relationship between the TiO$_2$ content in % by weight, based on the total weight of TiO$_2$ and synthetic mica, and the average layer thickness of the TiO$_2$ coating is preferably as follows:

a TiO$_2$ content from a range of 50.5-62% by weight with an average TiO$_2$ layer thickness from a range from above 20 to 35 nm;

a TiO$_2$ content from a range of 61-74% by weight with an average TiO$_2$ layer thickness from a range from above 35 to 45 nm;

a TiO$_2$ content from a range of 65.5-78% by weight with an average TiO$_2$ layer thickness from a range from above 45 to 55 nm;

a TiO$_2$ content from a range of 69.5-82% by weight with an average TiO$_2$ layer thickness from a range from above 55 to 65 nm;

a TiO$_2$ content from a range of 72.5-85% by weight with an average TiO$_2$ layer thickness from a range from above 65 to 75 nm;

a TiO$_2$ content from a range of 75-86.5% by weight with an average TiO$_2$ layer thickness from a range from above 75 to 85 nm;

a TiO$_2$ content from a range of 77.5-88% by weight with an average TiO$_2$ layer thickness from a range from above 85 to 95 nm;

a TiO$_2$ content from a range of 79-89% by weight with an average TiO$_2$ layer thickness from a range from above 95 to 105 nm;

a TiO$_2$ content from a range of 80.5-90% by weight with an average TiO$_2$ layer thickness from a range from above 105 to 115 nm;

a TiO$_2$ content from a range of 82-91% by weight with an average TiO$_2$ layer thickness from a range from above 115 to 125 nm;

a TiO$_2$ content from a range of 83-92% by weight with an average TiO$_2$ layer thickness from a range from above 125 to 135 nm;

a TiO$_2$ content from a range of 84.5-92.5% by weight with an average TiO$_2$ layer thickness from a range from above 135 to 145 nm;

a TiO$_2$ content from a range of 85.5-93% by weight with an average TiO$_2$ layer thickness from a range from above 145 to 155 nm;

a TiO$_2$ content from a range of 86.5-93% by weight with an average TiO$_2$ layer thickness from a range from above 155 to 165 nm;

a TiO$_2$ content from arrange of 87-93.5% by weight with an average TiO$_2$ layer thickness from a range from above 165 to 175 nm;

a TiO$_2$ content from a range of 88-94% by weight with an average TiO$_2$ layer thickness from a range from above 175 to 185 nm;

a TiO$_2$ content from a range of 88.5-94% by weight with an average TiO$_2$ layer thickness from a range from above 185 to 195 nm;

a TiO$_2$ content from a range of 89-94.5% by weight with an average TiO$_2$ layer thickness from a range from above 195 to 205 nm;

a TiO$_2$ content from a range of 89.5-95% by weight with an average TiO$_2$ layer thickness from a range from above 205 to 215 nm.

With very particular preference, the relationship between TiO$_2$ content in % by weight, based on the total weight of TiO$_2$ and synthetic mica, and the average layer thickness of the TiO$_2$ coating is as follows:

a TiO$_2$ content of 35-62% by weight with an average TiO$_2$ layer thickness of above 20 to 35 nm;

a TiO$_2$ content of 40-74% by weight with an average TiO$_2$ layer thickness of above 35 to 45 nm;

a TiO$_2$ content of 45-78% by weight with an average TiO$_2$ layer thickness of above 45 to 55 nm;

a TiO$_2$ content of 50-82% by weight with an average TiO$_2$ layer thickness of above 55 to 65 nm;

a TiO$_2$ content of 55-85% by weight with an average TiO$_2$ layer thickness of above 65 to 75 nm;

a TiO$_2$ content of 60-86.5% by weight with an average TiO$_2$ layer thickness of above 75 to 85 nm;

a TiO$_2$ content of 65-88% by weight with an average TiO$_2$ layer thickness of above 85 to 95 nm;

a TiO$_2$ content of 67-89% by weight with an average TiO$_2$ layer thickness of above 95 to 105 nm;

a TiO$_2$ content of 68-90% by weight with an average TiO$_2$ layer thickness of above 105 to 115 nm;

a TiO$_2$ content of 69-91% by weight with an average TiO$_2$ layer thickness of above 115 to 125 nm;

a TiO$_2$ content of 70-92% by weight with an average TiO$_2$ layer thickness of above 125 to 135 nm;

a TiO$_2$ content of 71-92.5% by weight with an average TiO$_2$ layer thickness of above 135 to 145 nm.

With more particular preference, the relationship between the TiO$_2$ content in % by weight, based on the total weight of TiO$_2$ and synthetic mica, and the average layer thickness of the TiO$_2$ coating is as follows:

a TiO$_2$ content of 47.5-62% by weight with an average TiO$_2$ layer thickness of above 20 to 35 nm;

a TiO$_2$ content of 58-74% by weight with an average TiO$_2$ layer thickness of above 35 to 45 nm;

a TiO$_2$ content of 63-78% by weight with an average TiO$_2$ layer thickness of above 45 to 55 nm;

a TiO$_2$ content of 67-82% by weight with an average TiO$_2$ layer thickness of above 55 to 65 nm;

a TiO$_2$ content of 70-85% by weight with an average TiO$_2$ layer thickness of above 65 to 75 nm;

a TiO$_2$ content of 73.5-86.5% by weight with an average TiO$_2$ layer thickness of above 75 to 85 nm;

a TiO$_2$ content of 75-88% by weight with an average TiO$_2$ layer thickness of above 85 to 95 nm;

a TiO$_2$ content of 76.5-89% by weight with an average TiO$_2$ layer thickness of above 95 to 105 nm;

a TiO$_2$ content of 78.5-90% by weight with an average TiO$_2$ layer thickness of above 105 to 115 nm;

a TiO$_2$ content of 80-91% by weight with an average TiO$_2$ layer thickness of above 115 to 125 nm;

a TiO$_2$ content of 81.5-92% by weight with an average TiO$_2$ layer thickness of above 125 to 135 nm;

a TiO$_2$ content of 83-92.5% by weight with an average TiO$_2$ layer thickness of above 135 to 145 nm.

The inventors have surprisingly found that pearlescent Pigments in which the fraction of TiO$_2$ and the layer thickness per synthetic mica substrate comply with the above relations have an outstanding soft-focus effect and are extremely suitable for use in cosmetics. These pearlescent pigments, structurally, feature a very high $TiO_2$ content per pearlescent pigment particle. In comparison to conventional pearlescent pigment particles, therefore, the fraction of $TiO_2$, based on the synthetic mica substrate, is significantly increased.

In a further preferred embodiment, the relationship between the $Fe_2O_3$ content in % by weight, based on the total weight of $Fe_2O_3$ and synthetic mica, and the average layer thickness of the $Fe_2O_3$ coating is preferably as follows:

an $Fe_2O_3$ content of 47.5-72.4% by weight with an average $Fe_2O_3$ layer thickness of above 35 to 45 nm;

an $Fe_2O_3$ content of 57.5-82.4% by weight with an average $Fe_2O_3$ layer thickness of above 45 to 55 nm;

an $Fe_2O_3$ content of 62.5-87.4% by weight with an average $Fe_2O_3$ layer thickness of above 55 to 65 nm.

The pearlescent pigments of the invention are notable structurally as well for a very high $Fe_2O_3$ content per pearlescent pigment.

In a further embodiment, the pearlescent pigments possess a total lead content ≤10 ppm, preferably from a range from 0.0 ppm to ≤9 ppm, more preferably from a range from 0.0 ppm to ≤8 ppm, more preferably still from a range from 0.1 ppm to ≤7 ppm, and with particular preference from a range from 0.1 ppm to ≤6.5 ppm.

The lead content is determined here by way of solids graphite tube atomic absorption spectrometry. The instrument used is preferably a ZEENIT 650 with SSA 600 solids sampler (manufacturer: Analytik Jena).

Instances of contamination by heavy metals in cosmetic formulations are unwanted in the interests of the consumer. Elevated lead levels, in particular, in cosmetic formulations have come under criticism in more recent times. Color additives are monitored for their lead content by the FDA, and must not exceed a limit of 20 µg/g. Other cosmetic ingredients are subject, in terms of lead content, to the responsibility of the manufacturers (Nancy M. Hepp, William R. Mindak, John Cheng, *J. Cosmet. Sci.*, 60, 405-414 (July/August 2009)).

Soft-focus effect is a term used for the capacity of suitable particles to provide visual reduction of unevennesses in the human skin and also of the contrast, and to effect visual smoothing of creases. Suitable particles are incorporated into cosmetic products and applied as a cosmetic layer, to the skin, for example. The soft-focus effect occurs when the incident light, after passing through the cosmetic layer, is diffusely scattered through interaction with the particles disposed on the skin's surface.

Skin defects such as "crow's feet" or creases are apparent only when they show a contrast with the background. Creases in skin act like light traps, in which the incident light is reflected within the crease until, as a result of this multiple reflection, the light is almost entirely absorbed.

In contrast to the light surrounding skin, therefore, the creases are perceived by an observer as dark, non-reflecting areas.

Through the use of highly scattering particles, such as fine spheres, for example, the light is diffusely scattered before it impinges on the skin, and so the underlying skin defects become virtually invisible.

However, in order to obtain a natural appearance, the particles must ensure not only a maximum scattering intensity but also a high level of light transmission. The effect of this is that the natural shade of the skin is not altered or concealed, i.e., the natural complexion continues to remain visible to the viewer.

In order to obtain a soft-focus effect, the particles employed must meet the following boundary conditions:
a) maximum diffuse reflection
b) minimum directed reflection
c) maximum transmission.

The $TiO_2$-coated pearlescent pigments of the invention are also outstandingly suitable UV absorbers. By UV absorption is meant the entire loss of light which results on passage through a layer comprising UV absorbers. This loss of light is composed of the total reflection plus the total absorption.

$TiO_2$ layers, as is known, are strongly UV-reflecting and therefore one of the uses of pearlescent pigments is as UV absorbers. The pearlescent pigments of the invention, by virtue of the high $TiO_2$ content, are particularly suitable UV absorbers. Moreover, the high edge fraction of the fine pigments may have the effect of high UV absorption.

In accordance with one preferred development of the invention, the pearlescent pigments have at least one further protective layer on the optically active layer, preferably high-index layer.

The at least one further protective layer here may at least one metal oxide layer whose metal oxides are selected from the group consisting of $SiO_2$, $Al_2O_3$, cerium oxide, mixtures and/or combinations thereof. As a protective layer it is also possible to apply a plastics coating, such as a polyacrylate layer, for example.

Particularly preferred in this context are protective layers of $SiO_2$ or of cerium oxide in combination with $SiO_2$, as are described in EP 1 727 864 A1 and EP 1 682 622 A1.

In a further embodiment, the present invention encompasses a pearlescent pigment based on synthetic mica having a density $\rho_S$ and having at least one optically active coating with a density $\rho_M$, the synthetic mica having an average size $d_{50}$ from a range from 2.1 µm to 7.0 µm and an average height $h_S$ from a range from 40 nm to 100 nm, and the total lead content of the pearlescent pigments being 0.0 ppm to ≤9 ppm.

In a further embodiment, the present invention encompasses a pearlescent pigment based on synthetic mica having a density $\rho_S$ and having at least one optically active coating with a density $\rho_M$, the synthetic mica having an average size $d_{50}$ from a range from 2.0 µm to 8.0 µm and an average height $h_S$ from a range from 40 nm to 110 nm, the pearlescent pigments possessing a size distribution with a $d_{90}$ value from a range from 5.0 µm to 11.0 µm, and the total lead content of the pearlescent pigments being 0.0 ppm to ≤9 ppm.

In a further embodiment, the present invention encompasses a pearlescent pigment based on synthetic mica having a density $\rho_S$ and having at least one optically active coating with a density $\rho_M$, the synthetic mica having an average size $d_{50}$ from a range from 2.0 µm to 8.0 µm and an average height $h_S$ from a range from 40 nm to 110 nm and has an L* value ≥90, and the pearlescent pigments possessing a size distribution with a $d_{90}$ value from a range from 5.0 µm to 11.0 µm, and the total lead content of the pearlescent pigments being 0.0 ppm to ≤9 ppm.

In a further embodiment, the present invention encompasses a cosmetic formulation comprising pearlescent pigments based on synthetic mica having a density $\rho_S$ and having at least one optically active coating with a density $\rho_M$, the synthetic mica having an average size $d_{50}$ from a range from 2.0 µm to 8.0 µm and an average height $h_S$ from a range from 40 nm to 110 nm, and the total lead content of the pearlescent pigments being 0.0 ppm to ≤9 ppm.

In a further embodiment, the present invention encompasses a cosmetic formulation comprising pearlescent pigments based on synthetic mica having a density $\rho_S$ and having at least one optically active coating with a density $\rho_M$, the synthetic mica having an average size $d_{50}$ from a range from 2.5 µm to 6.0 µm and an average height $h_S$ from a range from 40 nm to 95 nm, and the total lead content of the pearlescent pigments being 0.0 ppm to ≤8 ppm.

In a further embodiment, the present invention encompasses a cosmetic formulation comprising pearlescent pigments based on synthetic mica having a density $\rho_S$ and having at least one optically active coating with a density $\rho_M$, the synthetic mica having an average size $d_{50}$ from a range from 2.0 µm to 8.0 µm and an average height $h_S$ from a range from 40 nm to 110 nm, and the overall cosmetic formulation possessing a lead content of ≤15 ppm.

In a further embodiment, the present invention encompasses an inkjet ink comprising pearlescent pigments based on synthetic mica having a density $\rho_S$ and having at least one optically active coating with a density $\rho_M$, the synthetic mica possessing an average height $h_S$ from a range from 40 nm to 110 nm and the pearlescent pigments having a size distribution with a $d_{90}$ value from a range from 5.0 µm to 11.0 µm.

The process of the invention for producing the pearlescent pigments of the invention comprises the following steps:

a) classifying the largely transparent platelet-shaped synthetic substrate, to give a substrate having an average height $h_S$ from a range from 40 nm to 110 nm, b) coating the classified largely transparent platelet-shaped synthetic substrate with at least one optically active, preferably high-index, layer, to give a pearlescent pigment having an average size $d_{50}$ from a range from 2.1 µm to 8.6 µm.

Alternatively the largely transparent platelet-shaped synthetic substrates may first be coated with at least one optically active, preferably high-index, layer, and the resulting pearlescent pigments may subsequently be classified by size.

The coating of the largely transparent platelet-shaped synthetic substrates in step b) takes place preferably after the size classification in step a).

Classifying the largely transparent, preferably transparent, platelet-shaped synthetic substrate may be done by means of various methods, such as gravity sedimentation, sedimentation in a decanter, sieving, use of a cyclone or hydrocyclone, spiral classification, or a combination of two or more of these methods. A method such as sieving, for example, may also be used in a plurality of successive steps.

The pearlescent pigments of the invention are used preferably in coating compositions, which are selected preferably from the group consisting of paints, printing inks, inkjet inks, toners, cosmetics, plastics, textiles, glass, enamel, and ceramic.

The coating composition of the invention is preferably a cosmetic which is selected from the group consisting of concealer sticks, body powder, face powder, compact and loose powder, face makeup, powder cream, cream makeup, emulsion makeup, wax makeup, foundation, mousse makeup, blusher, eye makeup such as eye shadow, mascara, eyeliners, liquid eyeliners, eyebrow pencils, lipcare sticks, lipsticks, lip gloss, lip liners, hair-styling compositions such as hair spray, hair-setting products, hair mousse, hair gel, hair wax, hair mascara, permanent and semipermanent hair colors, temporary hair colors, skincare compositions such as lotions, gels, emulsions, and nail varnish compositions.

The pearlescent pigments of the invention are used preferably as soft-focus pigment, more particularly in cosmetics.

The coating composition of the invention is preferably a cosmetic product comprising one of the pearlescent pigments of the invention. The cosmetic product of the invention here may be one of the cosmetics specified above.

In another embodiment the cosmetic formulation may have a lead content ≤15 ppm; preferably the lead content may be situated within a range from 0.0 ppm to 13 ppm; more preferably the lead content may be situated within a range from 1.0 ppm to 11 ppm; and with particular preference the lead content may be situated within a range from 2.0 ppm to 10 ppm.

The pearlescent pigments of the invention can also be used advantageously in blends with transparent and opaque white, chromatic, and black pigments and also with further effect pigments, such as metallic effect pigments, for example.

Determining the average layer thicknesses and their distribution or standard deviation of a substrate may take place—as is known in the prior art—by means of SEM measurements. For this purpose, the pearlescent pigments are incorporated into a varnish, applied to a base—of metal or card, for example—by spraying or knife drawdown, for example, and cured. A polished section of the cured varnish is then taken, and this polished section is examined by SEM, and the pigment particles are measured. In order to obtain statistically underpinned values, at least 100 pigment particles ought to be counted. For the purposes of this invention, the determination of the layer thickness of the substrate and of the optically active layer, of a metal oxide coating or of a semitransparent metal layer, for example, can take place by this method.

With this method it is important that the pearlescent pigments are oriented largely plane-parallel. By this is meant that around 90% of the pearlescent pigments deviate by not more than ±15° and preferably not more than ±10° from the average orientation.

If the orientation of the pearlescent pigments in the varnish film is poor, a significant measurement error is obtained. One reason for this is that the pearlescent pigments in the polished section are tilted by an azimuthal angle α with respect to the observer. Another reason is that, owing to the surrounding binder medium, the imaging obtained has no depth definition, and so this angle cannot be estimated. Accordingly, an image of the layer thickness is "seen" which is enlarged by a factor of 1/cos α. At relatively large angles, this factor causes a significant error. Depending on the size of the angle α, therefore, the layer thicknesses determined by this method may be too high.

For the purposes of this invention, the average substrate layer thickness $h_S$ is preferably determined in accordance with the process described below, in order to arrive at more precise results. In the process, the average substrate thickness is determined from the relationship between metal oxide content and the layer thickness of the metal oxide. Finer and, as will be shown below, primarily thinner substrates possess higher specific surface areas. When these thinner substrates are coated with a material, it is necessary, in order for the coating to achieve a defined layer thickness, for them to be coated with more material than thicker substrates (per unit weight). This translates to a higher specific amount of the coating material in the overall pearlescent pigment, i.e., a higher coating material content, based on the weight of substrate employed.

The process is based on the following model:
a) the pigments consist of cylinders (platelets) having a uniform radius $r_S$ and a uniform height $h_S$. Calculation consequently takes place from the outset with "average values".
b) The probability of the coating molecules depositing on the substrate is equally high everywhere. Consequently, there is no difference, for example, between margin or surface of the platelet layer thickness. As a result of this assumption, the coating forms a uniform layer thickness $d_M$ everywhere. The index M here stands for optically active coating, preferably metal oxide and/or metal. The uniform coating thickness is actually observed in SEM investigations on a large number of coated, platelet-shaped effect pigments.
c) Secondary precipitations of M are disregarded; in other words, all of the material of M is applied as a coating on the substrate.

The amount of the coating M is defined as follows:

$$c_M = 100 * \frac{m_M}{m_M + m_S} \quad (\text{eq. 1})$$

Here, $m_M$ is the mass of the coating and $m_S$ the mass of the substrate. These parameters may also be expressed via the densities and volumes:

$$c_M = 100 * \frac{\rho_M \cdot V_M}{\rho_M \cdot V_M + \rho_S \cdot V_S} \quad (\text{eq. 2})$$

Here, $\rho_S$ and $\rho_M$ are the densities of the substrate and of the coating. For the volume of the substrate, the following simple relationship applies (cylinder volume):

$$V_S = \pi r_S^2 h_S \quad (\text{eq. 3})$$

The volume of the coating material, $V_M$, is calculated by a model which is outlined in FIG. 1.

The volume of the deposited metal oxide is divided here in principle between the end faces and the margin, and is represented in three terms (see FIG. 1):

$$V_M = (V_{M,1} + V_{M,2} + V_{M,3}) \quad (\text{eq. 4})$$

$$V_M = \begin{bmatrix} 2\pi \cdot d_M (r_S)^2 + \left(\frac{4}{3}\pi \cdot d_M^1 + \pi^2 d_M^2 r_S\right) + \\ (\pi \cdot d_M^2 h_S + 2\pi \cdot r_S \cdot d_M \cdot h_S) \end{bmatrix} \quad (\text{eq. 5})$$

Here, $h_S$ is the average height of the substrate, $r_S$ is the average diameter of the substrate, and $d_M$ is the geometric height of the layer thickness of the metal oxide.

Combining these equations, finally, gives the following expression:

$$c_M = \frac{100}{1 + \frac{\rho_S}{\rho_M} * \frac{h_S \cdot r_S^2}{\left(\frac{4}{3}d_M^3 + (\pi \cdot r_S + h_S) \cdot d_M^2 + (2r_S^2 + 2r_S h_S) \cdot d_M\right)}} \quad (\text{eq. 6})$$

If this equation is resolved, in turn, for the average substrate thickness $h_S$, then the following expression is obtained:

$$h_S = \frac{\frac{4d_M^3}{3r_S^2} + \frac{\pi d_M^2}{r_S} + 2 \cdot d_M}{\frac{\rho_S}{\rho_M \cdot \left(\frac{100}{c_M} - 1\right)} - \left(\frac{d_M}{r_S}\right)^2 - 2 \cdot \frac{d_M}{r_S}} \quad (\text{eq. 7})$$

In the context of this invention, the average substrate thickness $h_8$ is defined preferably via this equation when the average geometric layer thickness $d_M$ is 40 nm to 180 nm. At higher layer thicknesses, the formula is imprecise, since the high content of the optically active coating material causes the amount $c_M$ to run to a limiting value. At low layer thicknesses, likewise, effective differentiation is impossible.

In a further embodiment, the layer structure of the pearlescent pigments can also be analyzed, for example, using polished sections and/or by means of ESCA (Electron Spectroscopy for Chemical Analysis) in conjunction with sputter profiles. Where the geometric layer thickness $d_M$ is situated outside of the stated range of 40 nm to 180 nm, the layer thicknesses are preferably determined on the basis of above-described polished sections.

The average radius of the substrate here is determined preferably via laser diffraction measurements on the pearlescent pigments, preferably by means of laser granulometry using the Cilas 1064 from Quantachrome. In that case the $d_{50}$ value of the cumulative size distribution curve is employed; the relationship which applies is then as follows:

$$d_{50}/2 = r_S \quad (\text{eq. 8})$$

The parameter $c_M$ is determined via analytical measurements. In this case it is preferable to carry out an XFA analysis (X-ray Fluorescence Analysis) on finely divided pigment material. If necessary, the pigment powder is comminuted beforehand in a mill or in a mortar in order to provide a uniform sample material. Alternatively, the pearlescent pigment may also be dissolved, for example, using hydrofluoric acid, and the XFA analysis then performed from the solution.

Moreover, the analytical amounts of substrate and optically active material may also be determined via ICP (Inductively Coupled Plasma).

For densities it is preferred to use literature values (Handbook Chemistry and Physics). Examples of typical values are as follows:

TABLE 1

Densities of common materials of pearlescent pigments

| Material | Density | Function |
|---|---|---|
| Synthetic mica | 2.8 | Substrate |
| $Al_2O_3$ | 4.0 | Substrate (predominantly) |
| $SiO_2$ | 2.2–2.7 | Substrate (predominantly) |
| $TiO_2$ (rutile) | 4.3 | Coating |
| $TiO_2$ (anatase) | 3.9 | Coating |
| $Fe_2O_3$ (hematite) | 5.2 | Coating |
| $Fe_3O_4$ (magnetite) | 5.2 | Coating |

Where hybrid layers of two or more high-index layers are used, the density of the coating can be calculated from the literature values weighted with the analytically obtainable weight ratios between the individual materials.

The layer thickness of the metal oxide, finally, can be determined for example, and preferably, via the color of the pearlescent pigment. The underlying physical formulae of the optical qualities of pearlescent pigments have been set out in C. Schmidt, M. Fritz "Optical Physics of Synthetic Interference Pigments" Kontakte (Darmstadt) 1992 (2) pp. 15-24.

The color in this case may also be determined by means of a suitable arithmetic program such as the "Filmstar" software from FTG Software Associates, USA. In this case it is necessary to use the optical constants (refractive index n and optionally absorption constant k) of the optically active layer in the range of the optical wavelengths (400 to 800 nm). Values of this kind are well known for the usual materials.

The layer thickness may additionally be determined on the basis of the color from the publicly available information. For example, for $TiO_2$-coated pearlescent pigments based on synthetic mica, the following known relationship applies:

TABLE 2

Typical colors and geometric layer thicknesses of pearlescent pigments

| | Coverage/average geometric layer | Color |
|---|---|---|
| Silver-white pearlescent pigments | $TiO_2$: 40-60 nm | silver |
| Interference pigments | $TiO_2$: 20-40 nm | pale blue |
| | $TiO_2$: 60-80 nm | yellow |
| | $TiO_2$ 80-100 nm | red |
| | $TiO_2$: 100-140 nm | blue |
| | $TiO_2$: 120-160 nm | green |
| | $TiO_2$: 280-320 nm | green (IIIrd order) |
| Color luster pigments | $Fe_2O_3$: 35-45 nm | bronze |
| | $Fe_2O_3$: 45-55 nm | copper |
| | $Fe_2O_3$: 55-65 nm | red |
| | $Fe_2O_3$: 65-75 nm | red-violet |
| | $Fe_2O_3$: 75-85 nm | red-green |

In the majority of cases the color is determined almost exclusively by the layer thickness of the high-index coating (F. Hofmeister, Farbe+Lack 95, 557 (1989)).

Particularly in the case of pearlescent pigments with a large standard deviation in the substrate thickness distribution, the coloration is largely dependent not on the average thickness of the substrate, but is instead determined largely by the layer thickness of the high-index layer.

If the substrate with its layer thickness is likewise, in a non-negligible way, to determine the interference color, then a more precise optical calculation must be employed. In this case, the layer thickness of the substrate and of the optically active layer, preferably of the high-index metal oxide layer, may be determined, for example, from the positions of the maxima and/or minima of the remission spectrum of the pearlescent pigments.

Should the pearlescent pigment have a hybrid coating of two or more high-index oxides, then the optical constants are to be calculated, in analogy to the density calculation, from a weighting from the analytically available weight ratios of the individual high-index oxides.

Where, in contrast, the pearlescent pigment has a combination of two high-index oxides, the model can be used nevertheless. In the case of the first coating with high-index metal oxide, eq. 7 can be used directly. In the case of the calculation of the second high-index oxide, however, the layer thickness of the first oxide must be taken into account.

The layer thickness of the optically active layer, preferably of the high-index metal oxide layer, may also be determined, moreover, by SEM counting on well-oriented cross sections of the pearlescent pigments.

Another method for determining the average substrate layer thickness involves preparing the thicknesses of the (coated) pearlescent pigments in accordance with the method described in WO 2004/087816 A2 and likewise subjecting them to SEM measurement. In this case, at least 100 pigment particles ought to be measured, in order to obtain meaningful statistics. Subsequently, the arithmetic average value is determined. This represents the average thickness of the pearlescent pigment, $d_{tot}$, and, of course:

$$d_{tot}=2d_M+h_S \qquad (eq.\ 9)$$

Starting from equation (7) it is possible, by means of equation 9, to eliminate $d_M$ and then resolve it for $h_S$. In this case it is possible, in good approximation, to disregard the higher terms of $h_S$ and hence to determine $h_S$ from the relationship between the amount of the optically active layer $c_M$ and the average total pigment layer thickness $d_{tot}$.

The method based on eq. 7 for determining the average substrate layer thickness may also be used generally for platelet-shaped effect pigments. These pigments possess a platelet-shaped substrate and also a coating. This platelet-shaped substrate also encompasses metal pigments.

In further embodiments according to the invention, the pearlescent pigments have at least one further low-index layer. This layer may be disposed between substrate and high-index layer, or on the high-index layer.

The examples which follow illustrate the invention, but without restricting it.

Examples 1a-c: $Tio_2$-Coated Synthetic Mica

Example 1α: Classifying of Synthetic Mica 1 kg of platelet-shaped synthetic mica of the 10-40 μm fraction (from Shantou F.T.Z. Sanbao Pearl Luster Mica Tech Co., Ltd. China) were admixed with 1000 mL of DI water (i.e., fully deionized water), and then delaminated in a laboratory edge-runner mill from American Cyanamid Company for approximately 30 minutes.

The resulting paste was subsequently brought with DI water to a 10% by weight solids content, and was then treated in a TD 200 laboratory dissolver from Pendraulik for 45 minutes. During this treatment it was ensured that, by cooling, the temperature of the suspension did not exceed 80° C.

The mica suspension was then diluted with DI water to 3% by weight solids content and settled using a sedimentation vessel for 5 hours. The supernatant was drawn off by suction, and the sediment was again taken up with water, stirred up vigorously, and again settled for 5 hours. This operation was repeated a total of four times, until there was virtually no longer any supernatant apparent.

The sedimentation vessel possessed a cylindrical shape with the following dimensions: d=50 cm; h=50 cm.

The platelet-shaped synthetic mica originating from the supernatants was collected in a large container and induced to settle by addition of NaCl. After approximately 48 hours, the clear supernatant salt solution was drawn off by suction and the filter cake obtained was used as starting material for further coatings.

In this way, an extremely fine platelet-shaped synthetic mica is obtained with a $d_{50}$=3.4 μm (Cilas 1064) of the volume-averaged particle size distribution and also with an average thickness $h_S$ (from SEM)=79 nm.

Example 1a: Interference, Silver 100 g of platelet-shaped synthetic mica from example 1α (solids content: 42.3% by weight) were suspended in 200 mL of DI water. A pH of 2.2 was set by metered addition of dilute hydrochloric acid, and the suspension was heated to 80° C. Then 50 mL of a tin chloride solution with c(Sn)=24 g/L were metered in over 90 minutes. The pH was held constant at 2.2 by simultaneous introduction of a 15% by weight strength aqueous alkaline earth metal hydroxide solution. After an interruption of about ¼ h, during which the solution was stirred further, its pH was adjusted to 1.8 by metered addition of dilute hydrochloric acid. Subsequently, the addition was commenced of 2.4 L of a solution of 150 g of $TiCl_4$ and 50 g of HCl per liter. The pH was kept constant by simultaneous introduction of a 15% by weight strength aqueous alkaline earth metal hydroxide solution.

At the end of the addition, a silver pearlescent pigment was obtained. The suspension was stirred for a further hour, cooled, filtered with suction through a Büchner funnel, and washed with DI water until virtually ion-free.

Finally, the pearlescent pigment was calcined at 800° C. for 20 minutes.

Example 1b: Interference, Red 100 g of platelet-shaped synthetic mica from example 1α (solids content: 42.3% by weight) were suspended in 200 mL of DI water. A pH of 2.2 was set by metered addition of dilute hydrochloric acid, and the suspension was heated to 80° C. Then 50 mL of a tin chloride solution with c(Sn)=24 g/L were metered in over 90 minutes. The pH was held constant at 2.2 by simultaneous introduction of a 15% by weight strength aqueous alkaline earth metal hydroxide solution. After an interruption of about ¼ h, during which the solution was stirred further, its pH was adjusted to 1.8 by metered addition of dilute hydrochloric acid. Subsequently, the addition was commenced of 5.6 L of a solution of 150 g of $TiCl_4$ and 50 g of HCl per liter. The pH was kept constant by simultaneous introduction of a 15% by weight strength aqueous alkaline earth metal hydroxide solution.

At the end of the addition, a deep red pearlescent pigment was obtained. The suspension was stirred for a further hour, cooled, filtered with suction through a Büchner funnel, and washed with DI water until virtually ion-free.

Finally, the pearlescent pigment was calcined at 800° C. for 20 minutes.

Example 1c: Interference, Blue, 2nd Order 100 g of platelet-shaped synthetic mica from example 1α (solids content: 42.3% by weight) were suspended in 200 mL of DI water. A pH of 2.2 was set by metered addition of dilute hydrochloric acid, and the suspension was heated to 80° C. Then 50 mL of a tin chloride solution with c(Sn)=24 g/L were metered in over 90 minutes. The pH was held constant at 2.2 by simultaneous introduction of a 15% by weight strength aqueous alkaline earth metal hydroxide solution. After an interruption of about ¼ h, during which the solution was stirred further, its pH was adjusted to 1.8 by metered addition of dilute hydrochloric acid. Subsequently, the addition was commenced of 7.2 L of a solution of 150 g of $TiCl_4$ and 50 g of HCl per liter. The pH was kept constant by simultaneous introduction of a 15% by weight strength aqueous alkaline earth metal hydroxide solution.

At the end of the addition, a deep blue pearlescent pigment was obtained. The suspension was stirred for a further hour, cooled, filtered with suction through a Büchner funnel, and washed with DI water until virtually ion-free.

Finally, the pearlescent pigment was calcined at 800° C. for 20 minutes.

Comparative Example 1: Interference, Silver

Commercially available $TiO_2$-coated silver pearlescent pigment SunShine Super White from SunChemical.

Example 2: Bronze 100 g of platelet-shaped synthetic mica from example 1α (solids content: 42.3% by weight) were suspended in 200 mL of DI water. A pH of 2.9 was set by metered addition of dilute hydrochloric acid, and the suspension was heated to 75° C. Then, with a metering rate of 150 mL/h, an iron sulfate solution was added which contained 65 g of $Fe_2(SO_4)_3 \times 9H_2O$ and 1 mL of concentrated sulfuric acid per 100 mL of solution. The pH was held at 3.8 by simultaneous metered addition of a 15% by weight strength aqueous alkaline earth metal hydroxide solution. The iron hydroxide was obtained as a brownish precipitate, and undergoes deposition on the pigment particles.

Following addition of 1500 mL of $Fe_2(SO_4)_3$ solution, the covering was broken off, followed by stirring at reaction temperature for 1 hour, cooling, suction using a Büchner funnel, and washing with DI water to a virtually ion-free state.

The pearlescent pigment was calcined at 780° C. for 20 minutes.

The pearlescent pigment thus obtained possessed bronze color characteristics with a good luster and with a high scattering density at the same time.

APPLICATIONAL EXAMPLES

Example 3: Body Lotion

| INCI name | Product name | % by weight | Supplier |
|---|---|---|---|
| Phase A | | | |
| Water | | 81.20 | |
| Carbomer | Acritamer 934 | 0.50 | www.ritacorp.com |
| Propylene Glycol | 1,2-Propanediol | 2.75 | www.vwr.com |
| Glycerin | Pricerine 9090 | 0.50 | www.uniqema.com |
| Phase B | | | |
| | as per Ex. 1a (silver) | 2.00 | |
| Isopropyl Palmitate | Rita IPP NF | 2.00 | www.ritacorp.com |
| Glyceryl Stearate | Imwitor 960 K | 2.00 | www.sasolwax.com |
| Stearic Acid | Kortacid 1895 | 2.00 | www.akzonobel.com |
| *Butryospermum Parkii* Butter (Shea Butter) | Shea Butter | 2.00 | www.jandekker.com |
| Cetyl Alcohol | Cetyl Alcohol | 1.00 | www.vwr.com |
| Cyclomethicone | Dow Corning 345 Fluid | 0.20 | www.dowcorning.com |
| Dimethicone | Dow Corning 200 Fluid/350 cst | 0.20 | www.dowcorning.com |

-continued

| INCI name | Product name | % by weight | Supplier |
|---|---|---|---|
| Isostearyl Lactate | Patlac IL | 2.00 | www.ritacorp.com |
| Methylparaben, Propylparaben | Rokonsal SSH-1 | 0.30 | www.biochema.com |
| Tocopheryl Acetate | DL-Alpha-Tocopherol acetate | 0.10 | www.roche.com |
| Phase C | | | |
| Triethanolamine | Triethanolamine | 0.75 | www.vwr.com |
| Panthenol | D-Panthenol 75 L | 0.50 | www.basf.com |
| Fragrance | Palma Energy DF05 | q.s. | www.bell-europe.com |

The amount of pearlescent pigment used can be varied in a range from 0.1% by weight to 5.0% by weight. This variation can be compensated by a corresponding increase or reduction in the amount of water added. Phase A and phase B were heated separately to 80° C. with stirring. Phase B was then added slowly to the water phase, with stirring. The mixture was cooled to 50° C. and phase C was added. Stirring was then continued until room temperature was reached.

Example 4: Hair Mascara

| INCI name | Product name | % by weight | Supplier |
|---|---|---|---|
| Phase A | | | |
| Polyquaternium-16 | Luviquat FC 905 (Luviquat Exellence) | 2.70 | www.basf.com |
| Propylene Glycol | 1,2-Propanediol | 1.80 | www.vwr.com |
| Methylparaben | Methyl 4-hydroxybenzoate | 0.20 | www.sigmaaldrich.com |
| Water | | 64.45 | |
| Phase B | | | |
| Cetearyl Alcohol | Lanette O | 5.00 | www.cognis.com |
| Dimethicone | Dow Corning 200 Fluid/350 cst | 1.00 | www.dowcorning.com |
| Ceteareth-25 | Cremophor A 25 | 2.00 | www.basf.com |
| Propylparaben | Propyl 4-hydroxybenzoate | 0.10 | www.sigmaaldrich.com |
| Phase C | | | |
| Hydroxypropylcellulose | Klucel G | 0.50 | www.herc.com |
| Magnesium Aluminium Silicate | Veegum HV | 0.50 | www.rtvanderbilt.com |
| Water | | 19.00 | |
| Phase D | | | |
| | as per Ex. 2 (bronze) | 2.50 | |
| Phenoxyethanol (and) Methylparaben (and) Butylparaben (and) Ethylparaben (and) Propylparaben (and) Isobutylparaben | Phenonip | 0.20 | www.clariant.com |
| Fragrance | Blue Shadow ÖKO | 0.05 | www.bell-europe.com |

The amount of pearlescent pigment used can be varied in a range from 0.5% by weight to 10.0% by weight. This variation can be compensated by a corresponding increase or reduction in the amount of water added. Phase A and phase B were heated separately to 80° C., after which phase B was added slowly to phase A. In a separate vessel, Klucel and Veegum were added to the water of phase C, with stirring. Then phase AB was cooled to 40° C. and, during the cooling procedure, phases C and D were mixed in with stirring.

Example 5: Lip Gloss

| INCI name | Product name | % by weight | Supplier |
|---|---|---|---|
| Phase A | | | |
| Hydrogenated Polyisobutene (and) Ethylene/Propylene/Styrene Copolymer (and) Butylene/Ethylene/Styrene Copolymer | Versagel ME 750 | ad 100 | www.penreco.com |
| Simmondsia Chinensis (Jojoba) Seed Oil | Jojoba Oil-Natural/Golden | 2.00 | www.biochemica.com |
| Caprylyl Trimethicone | Silcare Silicone 31M50 | 7.00 | www.clariant.com |
| Stearyl Dimethicone | Silcare Silicone 41M65 | 3.20 | www.clariant.com |
| Hydrogenated Polydecene | Nexbase 2002 | 4.00 | www.jandekker.com |
| Isopropyl Myristate | Isopropyl Myristate | 4.50 | www.vwr.com |
| Phase B | | | |
| | as per Ex. 1a (silver) | 5.00 | |
| Propylparaben | Propyl 4-hydroxybenzoate | 0.20 | www.sigmaaldrich.com |

The amount of pearlescent pigment used can be varied in a range from 0.1% by weight to 8.0% by weight. This variation can be compensated by a corresponding increase or reduction in the amount of Versagel ME 750 added.

Phase A was heated to 85° C., and then the ingredients of phase B were added individually to phase A and the mixture was stirred until the consistency was uniform, at which point it was filled into a lip gloss container.

Example 6: Pressed Eye Shadow

| INCI name | Product name | % by weight | Supplier |
|---|---|---|---|
| Phase A | | | |
| Mica | Silk Mica | 17.00 | www.vwr.com |
| Boron Nitride | Softouch CCS 102 | 2.50 | www.advceramicscos.com |
| Zinc Stearate | Kemilub EZ-V | 7.00 | www.undesa.com |
| Talc | Talc Powder | 38.50 | www.riedeldehaen.com |
| | as per Ex. 1a (silver) | 25.00 | |

-continued

| INCI name | Product name | % by weight | Supplier |
|---|---|---|---|
| Phase B | | | |
| Dimethicone | Dow Corning ® 200 Fluid 5 cst | 5.00 | www.dowcorning.com |
| Cyclomethicone (and) Dimethicone Crosspolymer | Dow Corning ® 9040 Elastomer | 5.00 | www.dowcorning.com |

The amount of pearlescent pigment used can be varied in a range from 5.0% by weight to 40.0% by weight. This variation can be compensated by a corresponding increase or reduction in the amount of mica added. Phase A was mixed in a high-speed mixer at 2500 rpm for 30 seconds. Then phase B was added and the mixture was mixed in the same mixer at 3000 rpm for 60 seconds. Lastly the powder mixture was press-shaped for 30 seconds at 150 bar by means of an eye shadow press.

Example 7: Lipstick

| INCI name | Product name | % by weight | Supplier |
|---|---|---|---|
| Phase A | | | |
| Carnauba Wax | Ewacera 34 | 4.50 | www.wagnerlanolin.de |
| Bees Wax | Ewacera 12 | 3.50 | www.wagnerlanolin.de |
| Candelilla Wax | Ewacera 42 | 4.00 | www.wagnerlanolin.de |
| Microcrystalline Wax | Parcera MW | 7.20 | www.paramelt.com |
| Cetyl Palmitate | Walrath synthetic | 2.00 | www.kahlwax.de |
| Hydrogenated Coco-Glycerides | Softisan 100 | 5.00 | www.sasolwax.com |
| Petrolatum | Penreco Blond | 5.80 | www.penreco.com |
| Cetearyl Octanoate | Luvitol EHO | 10.70 | www.basf.com |
| Tocopheryl Acetate | D,L-Alpha Tocopherol acetate | 0.50 | www.dsm.com |
| Castor Oil | Castor Oil | 36.60 | www.riedeldahaen.com |
| Phase B | | | |
| Mica (and) Iron Oxide | Prestige Fire-red | 16.00 | www.eckart.net |
|  | As per Ex. 1a (silver) | 4.00 | |
| Methylparaben, Propylparaben | Rokonsal SSH-1 | 0.20 | www.biochema.com |

The amount of pearlescent pigment used can be varied in a range from 0.5% by weight to 10.0% by weight. Compensation can be made with other pigments; the level of pigmentation must be maintained at 21% by weight. Phase A was heated to 85° C., after which phase B was added to phase A and mixing took place. The mixture was subsequently, at a temperature of 75° C., filled into a lipstick mold.

I Physical Characterization

Ia Particle Size Measurement

The pigments of the inventive examples and comparative example, and also the synthetic mica from example 1α, were characterized by means of laser diffraction methods (instrument: Cilas 1064, Quantachrome). The scattered light signals were evaluated by the Fraunhofer method.

For this purpose, approximately 50 mL of pearlescent pigment suspension or synthetic mica suspension (nonvolatile content approximately 35% by weight) were mixed with 50 mL of isopropanol, using a magnetic stirrer, and then treated for 300 seconds in a Sonorex IK 52 ultrasound bath from Bandelin. 2.5 mL of sample were then pipetted into the instrument for measurement.

The $d_{50}$ values of the volume-averaged cumulative frequency distribution are shown in table 3 (column 8).

Ib Determination of the Average Thickness of the Substrate

The average substrate thickness was determined by various methods. The results are set out in table 3.

a) The pearlescent pigments were incorporated at 10% by weight into an Autoclear Plus HS 2-component clearcoat from Sikkens GmbH, using a sleeve brush, then applied to a film, using a wire-wound coating bar (26 µm wet film thickness), and dried. After a drying time of 24 hours, polished sections were prepared of these knife drawdowns. The polished sections were measured by SEM. For each sample here, at least 100 pigment particles were measured, in order to obtain meaningful statistics. Not only the substrate layer thickness but also the layer thickness of the metal oxide layer was determined in this case.

b) The pearlescent pigments were prepared by the method described in WO 2004/087816 A2 and likewise measured by SEM. The results are shown in table 3 in column 10.

c) The average substrate height was calculated by eq. 7. In this case, for the substrate radius, half of the $d_{50}$ values of the volume-averaged size distribution was used.

The amounts of $TiO_2$ and of $Fe_2O_3$ and also of substrate material were determined by means of XFA (X-ray Fluorescence Analysis).

For this purpose, the pearlescent pigment powder was introduced directly from the bed into a sample container covered with a 6 µm polypropylene film (from Fluxana), and was measured from this container. The measuring instrument used was the Advant-X instrument from Thermo ARL.

The metal oxide contents according to eq. 1 are set out in table 3 in column 4 in % by weight based on metal oxide and substrate.

Finally, it was necessary also to determine the layer thickness of $TiO_2$ and $Fe_2O_3$. Here, the factors used for the work were the colors of the pigments and the usual layer thicknesses published in the literature for them. These oxide layer thicknesses are listed in table 3 in column 6, in nm.

The values calculated according to eq. 7 are listed in table 3 in column 9, in nm.

TABLE 3

Physical characterization of the examples

| Sample | Substrate | Metal oxide | Amount of metal oxide (eq. 1) in % | Color | Layer thickness of metal oxide/nm from color | Layer thickness of metal oxide/nm from SEM | $d_{50}$ [µm] (instrument: Cilas 1064) | $h_s$ [nm] as per eq. 7 | $h_s$ from SEM on the mica [nm] Powder | $h_s$ from SEM on the mica [nm] Polished section | $h_s$ from SEM on pearlescent in the section [nm] |
|---|---|---|---|---|---|---|---|---|---|---|---|
| Example 1a | Mica as per Ex. 1α | TiO$_2$ | 64.0 | silver | 50 | 53 | 3.6 | 95 | 79 | 90 | 114 |
| Example 1b | Mica as per Ex. 1α | TiO$_2$ | 79.1 | red | 90 | 89 | 3.8 | 81 | | | 111 |
| Example 1c | Mica as per Ex. 1α | TiO$_2$ | 82.9 | blue | 130 | 131 | 3.9 | 96 | | | |
| Example 2 | Mica as per Ex. 1α | Fe$_2$O$_3$ | 66.1 | bronze | 40 | 42 | 3.7 | 82 | 79 | 90 | 112 |

Results of the Layer Thickness Determinations

Good agreements are found for the values calculated by eq. 7, via the oxide contents and oxide layer thicknesses, with the average layer thicknesses found in accordance with the evaluation of the vertically oriented powders of the mica (column 10) and of the mica in the knife drawdown.

These findings suggest the consistency of the model of eq. 1-7 and the reliability of the determination of the average layer thickness by this method.

The determination of the average layer thickness of the mica from the polished sections (column 11) systematically shows higher values in comparison to the determination on vertically oriented powders. This is probably attributable essentially to the fact that the pigments of the polished-section method have somewhat different orientations of the platelets within the varnish.

The determination of the average layer thickness $h_S$ from the polished sections of the pearlescent pigments (column 12) themselves leads to values which potentially are higher still.

Therefore, in the context of this invention, the average substrate layer thickness is ascertained preferably by eq. 7 when the average geometric layer thicknesses of the optically active layer are 40 nm to 180 nm.

II Tests:

IIa Angle-Dependent Lightness Measurements

In order to characterize the reflective scattered-light fraction, the pearlescent pigment was incorporated with stirring, at a level of pigmentation of 6% by weight, based on the total weight of the wet varnish, into a conventional nitrocellulose varnish (Dr. Renger Erco Bronzemischlack 2615e; from Morton). The pearlescent pigment was introduced and then dispersed into the varnish with a brush.

The completed varnish was applied, on a knife drawdown apparatus (wire-wound coating bar) with a wet film thickness of 50 µm, to #2853 test charts from Byk Gardner (contrast paper).

Using the MA 68II multi-angle colorimeter from X-Rite, the L* value was determined with a constant incident angle of 45° (as per manufacturer specifications) and an observation angle of 110° relative to the specular angle.

Strongly reflecting samples (ideal mirror case) reflect virtually the entire incident light at what is called the specular angle. Accordingly, the greater the distance from the specular angle in the measurement, the less light and hence the lightness (L*) that can be measured. Within the coatings industry, this effect, which occurs preferentially with metallic pigments, is described as lightness flop.

The situation is different with strongly scattering samples. Here, the incident light is reflected, ideally uniformly, over all angles. Accordingly, considerable lightness values ought still to be detectable even at measurement angles far removed from the specular angle. Suitable above all for the characterization here is the 110° angle.

IIb Gloss Measurements:

The scattering nature of the respective sample can be characterized additionally through the measurement of the gloss. The gloss is a measure of the directed reflection. Strongly scattering samples, therefore, ought to have a low gloss. The nitrocellulose varnish applications from IIa were subjected to measurement using a Micro-Tri-Gloss gloss meter from Byk Gardner with a measurement angle of 60° against a black background.

IIc Opacity

The pearlescent pigments of the invention and the comparative example were applied at different concentrations onto #2853 test charts from Byk Gardner (contrast paper) as per II a, and the opacity was compared visually. This opacity was assessed on the basis of the following ratings:

1=very poor
2=poor
3=moderate
4=good
5=very good

IId Determination of Lead Content

The lead content was determined via solids graphite tube atomic absorption spectrometry. The instrument used was ZEENIT 650 with SSA 600 solids sampler (manufacturer: Analytik Jena). The lead contents of the pearlescent pigments of the invention can be seen in table 4.

TABLE 4

Results of the optical measurements, opacity, and lead content

| Interference color | Sample | Opacity (visual) | L* 110° | Gloss 60° | Lead content [ppm] |
|---|---|---|---|---|---|
| silver | Example 1a | 4 | 38.9 | 9.9 | <1 |
| red | Example 1b | 4 | | | <1 |
| blue | Example 1c | 4 | 37.5 | 6.4 | <1 |
| bronze | Example 2 | 5 | 22.7 | 11.5 | <1 |
| silver | Comparative example 1 | 2 | 13.1 | 55.8 | 16 |

The pearlescent pigments of the invention have a consistently better opacity than the comparative example from the prior art.

Furthermore, the pearlescent pigments of the inventive examples exhibit a lower gloss than the comparative example of the corresponding shade. The directed reflection here is evidently lower. This is entirely desirable for a soft-focus effect.

In the same way, the $L_{110°}$ values for the inventive examples are substantially higher than for the corresponding comparative example. The measurements show that the inventive examples evidently have a higher scattered-light fraction.

This is probably attributable to the low particle size and the low substrate layer thickness. The low particle size of the synthetic mica goes hand in hand with an increased edge fraction and hence with greater scattering. The lower substrate layer thickness leads in turn to a substantially increased $TiO_2$ content at comparable layer thickness. The high-index $TiO_2$ commonly does not fall in a perfect smooth layer, but instead always has a certain particle size distribution. These oxide particles always give rise to a certain scattering. It is thought that the higher scattered-light fraction of the samples according to the invention is also attributable to this effect.

Furthermore, the pearlescent pigments of the invention have a significantly lower lead content than comparative example 1.

IIe Measurement of the Soft-Focus Effect

For this purpose, the pearlescent pigments were incorporated with stirring, at a level of pigmentation of 2.5% by weight (based on the total weight of the wet varnish), into a conventional nitrocellulose varnish (Dr. Renger Erco Bronzemischlack 2615e; from Morton). The pearlescent pigment was in this case introduced and then dispersed into the varnish using a brush.

The completed varnish was applied on a commercial mechanical knife drawdown apparatus (wire-wound coating bar) with a wet film thickness of 50 μm to commercially available transparent PET films, e.g., Hostophan.

The films coated in this way were subjected to measurement for total transmission and haze using the Haze-gard plus from Byk Gardner. The haze is a product of what is called the large-angle scattering (according to ASTM D 1003, the haze is the amount of light which deviates on average by more than 2.5° from the incident light beam—measured in %).

Figure 2:
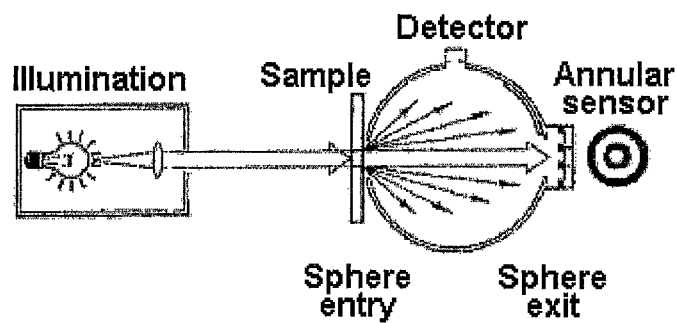
FIG. 2 is a diagram illustrating apparatus for measuring haze and total transmission for determining soft focus effect.

The measurement principle can be taken from FIG. 2.

A light bundle impinges on the sample and enters into an integrating sphere. The inside wall of the sphere has a matt white coating, in order to guarantee uniform distribution of the light. A detector in the sphere measures the total transmission with the sphere exit closed, and the haze with the sphere exit open.

In order to measure the directed reflection, the gloss of the respective films was determined using a Micro-Gloss instrument from Byk Gardener at an angle of 60° C.

TABLE 5

Measurement of the soft-focus effect

| Specimens | Transmission | Haze (% at >2.5°) | Gloss |
|---|---|---|---|
| Example 1a | 73.4 | 72.6 | 29.5 |
| Example 1b | 85.6 | 71.5 | 33.7 |

The measurement values from table 5 show that the pearlescent pigments of the invention possess a high transmittance. At the same time, however, these pearlescent pigments also have a very high scattered-light fraction (haze).

In the combination of properties, the pearlescent pigments of the invention meet important requirements for achieving a soft-focus effect in the application.

In addition, the pearlescent pigments claimed, in contrast to commercial soft-focus particles, combine the properties of a soft-focus pigment with those of a pearlescent pigment (interference shades, satin gloss), while at the same time having a low lead content.

The invention claimed is:

1. Pearlescent pigments comprising transparent platelet-shaped synthetic substrates having a density $\rho_S$ and at least one optically active coating having a density $\rho_M$,
   wherein the transparent platelet-shaped synthetic substrates are synthetic mica,
   wherein the $d_{50}$ value of the cumulative frequency distribution of the substrates volume-average size distribution obtained by, laser diffraction is within the range of 2.1 μm to 7.0 μm and an average height $h_S$ within the range of 40 nm to 110 nm, the standard deviation in the average height $h_S$ is from 25% to 80%, and the total lead content of the pearlescent pigments is ≤10 ppm by weight ratio,
   wherein the optically active coating comprises at least one metal oxide layer, and optionally at least one of a metal hydroxide layer(s) or a metal oxide hydrate layer(s), and
   wherein the metal oxide layer consists of metal oxides consisting of titanium oxide and optionally one or more of iron oxide, cerium oxide, chromium oxide, tin oxide, zirconium oxide, or cobalt oxide, the relationship between the titanium oxide content in % by weight, based on the total weight of titanium oxide and synthetic mica, and the average layer thickness of the metal oxide layer is as follows:
   a titanium oxide content of 30-80% by weight for an average metal oxide layer thickness of 20 nm to 50 nm;
   a titanium oxide content of 50-85% by weight for an average metal oxide layer thickness of greater than 50 nm to 75 nm;
   a titanium oxide content of 59-89% by weight for an average metal oxide layer thickness of greater than 75 nm to 95 nm;
   a titanium oxide content of 66-92% by weight with an average metal oxide layer thickness of greater than 95 nm to 125 nm; or
   a titanium oxide content of 69-96% by weight with an average metal oxide layer thickness of greater than 125 nm to 215 nm.

2. The pearlescent pigments of claim 1, wherein the pearlescent pigments have a size distribution with a $d_{90}$ value within the range of 5.0 μm to 11.0 μm.

3. The pearlescent pigments of claim 1, wherein the optically active coating is a high-index coating having a refractive index $n_M>2.0$.

4. The pearlescent pigments of claim 1, wherein the average substrates height $h_S$ is determined by the following formula:

$$h_S = \frac{\frac{4d_M^3}{3r_S^2} + \frac{\pi d_M^2}{r_S} + 2 \cdot d_M}{\frac{\rho_S}{\rho_M \cdot \left(\frac{100}{c_M} - 1\right)} - \left(\frac{d_M}{r_S}\right)^2 - 2 \cdot \frac{d_M}{r_S}}.$$

wherein the average geometric layer thickness of the optically active coating, $d_M$ is 40 nm to 180 nm, $r_S = d_{50}/2$ is the average radius of the substrates, determined via laser diffraction methods, $\rho_S$ is the density of the substrates and $\rho_M$ is the density of the optically active coating and $c_M$ is the weight fraction in % of the optically active coating, determined via analytical measurements, based on the total weight of substrates and optically active coating.

5. A method for producing the pearlescent pigments of claim 1, comprising:
   a) classifying transparent platelet-shaped synthetic substrates, in order to obtain substrates having a $d_{50}$ value of the cumulative frequency distribution of the substrates volume-average size distribution within the range of 2.1 μm to 7.0 μm, as determined by laser diffraction, an average height $h_S$ from a range of 40 nm to 110 nm, the standard deviation in the average height $h_S$ is from 25% to 80%, and the total lead content of the pearlescent pigments is ≤10 ppm by weight ratio; and
   b) coating the classified transparent platelet-shaped synthetic substrates obtained in a) with at least one optically active coating comprising at least one metal oxide layer, in order to obtain pearlescent pigments comprising transparent platelet-shaped synthetic substrates having a density $\rho_S$ and at least one optically active coating having a density $\rho_M$.

6. A coating composition comprising the pearlescent pigments of claim 1.

7. The pearlescent pigments of claim 1, wherein the titanium oxide is in the anatase modification.

8. The coating composition of claim 6, wherein the coating composition is a paint, printing ink, inkjet ink, toner, cosmetic, plastic, textile, glass, enamel, glaze or ceramic.

9. The coating composition of claim 6, wherein the coating composition is a cosmetic product.

10. A cosmetic product comprising the pearlescent pigments of claim 1.

11. A cosmetic product comprising the coating composition according to claim 6.

12. A method for providing a soft-focus effect to a coating composition, comprising:
   adding the pearlescent pigments of claim 1 to a coating composition.

13. The method according to claim 12, wherein the coating composition is a paint, printing ink, inkjet ink, toner, cosmetic, plastic, textile, glass, enamel, glaze or ceramic.

14. The pearlescent pigments of claim 1, wherein the transparent platelet-shaped synthetic substrates comprise an iron content within the range of 0.01% by weight to 0.2% by weight.

15. The pearlescent pigments of claim 1, wherein the metal oxide layer consists of titanium oxide and tin oxide.

16. The pearlescent pigments of claim 1, wherein the metal oxide layer consists of titanium oxide.

17. Pearlescent pigments comprising transparent platelet-shaped synthetic substrates having a density $\rho_S$ and at least one optically active coating having a density $\rho_M$,
   wherein the transparent platelet-shaped synthetic substrates are synthetic mica,
   wherein the $d_{50}$ value of the cumulative frequency distribution of the substrates volume-average size distribution obtained by, laser diffraction is within the range of 2.1 μm to 7.0 μm and an average height $h_S$ within the range of 40 nm to 110 nm, the standard deviation in the average height $h_S$ is from 25% to 80%, and the total lead content of the pearlescent pigments is ≤10 ppm by weight ratio,
   wherein the optically active coating comprises at least one metal oxide layer, and optionally at least one of a metal hydroxide layer(s) or a metal oxide hydrate layer(s), and
   wherein the metal oxide layer consists of iron oxide, and optionally one or more of cerium oxide, chromium oxide, tin oxide, zirconium oxide, or cobalt oxide, and the relationship between the $Fe_2O_3$ content in % by weight, based on the total weight of $Fe_2O_3$ and synthetic mica, and the average layer thickness of the metal oxide layer is as follows:
   a $Fe_2O_3$ content of 47.5-72.4% by weight for an average metal oxide layer thickness of 35 nm to 45 nm;
   a $Fe_2O_3$ content of 57.5-82.4% by weight for an average metal oxide layer thickness of 45 nm to 55 nm; or
   a $Fe_2O_3$ content of 62.5-87.4% by weight for an average metal oxide layer thickness of 55 nm to 65 nm.

18. The pearlescent pigments of claim 1, wherein the metal oxide layer consists of $Fe_2O_3$.

* * * * *

UNITED STATES PATENT AND TRADEMARK OFFICE
CERTIFICATE OF CORRECTION

PATENT NO. : 10,125,261 B2
APPLICATION NO. : 13/501497
DATED : November 13, 2018
INVENTOR(S) : Ulrich Schmidt et al.

Page 1 of 1

It is certified that error appears in the above-identified patent and that said Letters Patent is hereby corrected as shown below:

On the Title Page

Item (22) Column 1, PCT Filed, Line 1 delete "Oct. 10, 2010" and insert --Oct. 12, 2010--

In the Claims

Column 28, Lines 60-67, Claim 4, delete "
$$h_S = \frac{\frac{4d_M^3}{3r_S^2} + \frac{\pi d_M^2}{r_S} + 2 \cdot d_M}{\frac{\rho_S}{\rho_M \cdot \left(\frac{100}{c_M} - 1\right)} - \left(\frac{d_M}{r_S}\right)^2 - 2 \cdot \frac{d_M}{r_S}} \cdot$$
"

and insert --
$$h_S = \frac{\frac{4d_M^3}{3r_S^2} + \frac{\pi d_M^2}{r_S} + 2 \cdot d_M}{\frac{\rho_S}{\rho_M \cdot \left(\frac{100}{c_M} - 1\right)} - \left(\frac{d_M}{r_S}\right)^2 - 2 \cdot \frac{d_M}{r_S}},$$
 --

Signed and Sealed this
Twenty-sixth Day of February, 2019

Andrei Iancu
*Director of the United States Patent and Trademark Office*